US012064538B2

(12) United States Patent
Aelen et al.

(10) Patent No.: US 12,064,538 B2
(45) Date of Patent: Aug. 20, 2024

(54) PUMP ARRANGEMENT, CONFIGURED TO BE USED WITH A DOUBLE BREAST PUMP DEVICE

(71) Applicant: KONINKLIJKE PHILIPS N.V., Eindhoven (NL)

(72) Inventors: Paul Aelen, Eindhoven (NL); Johannes Petrus Antonius Maria Van Asseldonk, Best (NL); Arjan Teodor Van Wieringen, Malden (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 901 days.

(21) Appl. No.: 16/973,467

(22) PCT Filed: Jun. 26, 2019

(86) PCT No.: PCT/EP2019/066940
§ 371 (c)(1),
(2) Date: Dec. 9, 2020

(87) PCT Pub. No.: WO2020/007671
PCT Pub. Date: Jan. 9, 2020

(65) Prior Publication Data
US 2021/0369926 A1   Dec. 2, 2021

(30) Foreign Application Priority Data

Jul. 4, 2018 (EP) .................................... 18181685

(51) Int. Cl.
*A61M 1/06* (2006.01)
*A61M 1/00* (2006.01)

(52) U.S. Cl.
CPC ................ *A61M 1/06* (2013.01); *A61M 1/74* (2021.05); *A61M 1/06935* (2021.05); *A61M 1/0697* (2021.05); *A61M 2205/3337* (2013.01)

(58) Field of Classification Search
CPC ................ A61M 1/0693; A61M 1/069; A61M 1/06935; A61M 1/0697; A61M 1/06; A61M 1/062; A61M 1/74; A61M 2205/3337
See application file for complete search history.

(56) References Cited

U.S. PATENT DOCUMENTS 5,954,690 A    9/1999  Larsson
2005/0283112 A1*  12/2005  Britto ...................... A61M 1/06
                                                                604/74

FOREIGN PATENT DOCUMENTS

WO      03092768      11/2003
WO      2015029030    3/2015
(Continued)

OTHER PUBLICATIONS

International Search Report and Written Opinion Dated Sep. 17, 2019 For International Application No. PCT/EP2019/066940 Filed Jun. 26, 2019.

*Primary Examiner* — Emily L Schmidt
*Assistant Examiner* — Antarius S Daniel

(57) ABSTRACT

In a pump arrangement (6) for use with a double breast pump device, a first air conduit (65) and a second air conduit (66) have a function in connecting respective expression kits (2, 3) to the pump arrangement (6). Each of the air conduits (65, 66) N is connectable to and disconnectable from a suction side and a discharge side, respectively, of a pump (61) that is included in the pump arrangement (6). Further, the air conduits (65, 66) are connectable to and disconnectable from each other directly through an intermediate switching mechanism (70) arranged between the air conduits (65, 66) at a bypass position with respect to the pump (61), so that it is possible to directly transfer vacuum between the (Continued)

air conduits (65, 66) and to thereby support the functioning of the pump (61) which may be relatively small for that reason.

14 Claims, 2 Drawing Sheets

(56) References Cited

FOREIGN PATENT DOCUMENTS

| WO | 2016179580 | 11/2016 | | |
|---|---|---|---|---|
| WO | 2017/077029 | 5/2017 | | |
| WO | WO-2017077029 A1 * | 5/2017 | .......... | A61M 1/0035 |

\* cited by examiner

PUMP ARRANGEMENT, CONFIGURED TO BE USED WITH A DOUBLE BREAST PUMP DEVICE

CROSS REFERENCE TO RELATED APPLICATIONS

This application is the U.S. National Phase application under 35 U.S.C. § 371 of International Application No. PCT/EP2019/066940 filed Jun. 26, 2019, which claims the benefit of European Patent Application Number 18181685.1 filed Jul. 4, 2018. These applications are hereby incorporated by reference herein.

FIELD OF THE INVENTION

The invention relates to a pump arrangement, configured to be used with a double breast pump device comprising two expression kits, each expression kit being designed to subject a breast of a user of the device to a pressure profile and to receive milk expressed from the breast, the pump arrangement comprising: a pump configured to create the pressure profile in the expression kits, and a first air conduit and a second air conduit, each air conduit being designed to allow for air connection of an expression kit to the pump arrangement.

The invention also relates to a double breast pump device, comprising two expression kits, each expression kit being designed to subject a breast of a user of the device to a pressure profile and to receive milk expressed from the breast, and a pump arrangement as mentioned.

The invention further relates to a method of operating a pump arrangement of a double breast pump device comprising two expression kits, each expression kit being designed to subject a breast of a user of the device to a pressure profile and to receive milk expressed from the breast, the pump arrangement comprising a pump configured to create the pressure profile in the expression kits, and a first air conduit and a second air conduit, each air conduit being designed to allow for air connection of an expression kit to the pump arrangement.

BACKGROUND OF THE INVENTION

In general, a breast pump device is a well known tool for extracting milk from a breast of a user of the device, i.e. a lactating woman, or from two breasts simultaneously. Breast pump devices may be used in various situations, for example, if a baby or infant is not capable of extracting milk from the breast, or if a mother is separated from her baby or infant and the baby or infant is to be fed with breast milk at a later stage, by the mother or another person. Hence, breast pump devices are used by women to express breast milk at a convenient time, to be stored for later consumption by their/a baby or infant. Breast pump devices may also be helpful in a situation in which it is desired to stimulate and increase milk production in women with a low milk supply or to relieve pressure from engorged breasts.

A breast pump device is typically operated with one or two expression kits. A breast pump device that is designed to enable the use of two expression kits is referred to as double breast pump device. Among other things, an expression kit comprises a breast-receiving funnel for receiving a woman's breast, which funnel may be equipped with pads or the like for massaging the breast in a certain way, and is designed for connection to a vacuum unit for realizing a pressure cycle in the expression kit, by means of which milk expression from the breast is enabled. In practical cases, the vacuum unit comprises an electric vacuum pump device, but manually operated breast pump devices are also known and used in practice. The fact is that by generating a pressure cycle, particularly a vacuum cycle, possibly accompanied by a certain way of massaging the breast, a simulation of a feeding action is obtained, which triggers the necessary let-down reflex in the lactating woman using the breast pump device. For the sake of completeness, it is noted that the term "vacuum" as used in this text refers to a relatively low pressure, i.e. a pressure that is significantly lower than ambient pressure, and that is also referred to as underpressure.

US2005/0283112 discloses a portable pumping device for drawing milk from a human breast includes a breast shield adapted to fit over a nipple of a breast and a flow line coupled to the breast shield. The flow line is adapted to allow air to flow there through a pump coupled to the breast shield via the flow line. The pump includes a pump intake and a pump exhaust and is operable to create a pressure drop between the nipple and the pump, wherein the pressure drop creates a suction at the breast shield by lowering the pressure of air in the flow line. A blow-back valve is disposed between the flow line and the pump. The blow-back valve has a valve piston disposed in a valve housing The valve housing includes a flow line aperture that communicates via the flow line with the breast shield, a valve inlet adapted to communicate external to the flow line, and a valve exhaust adapted to communicate external to the flow line. The valve piston is adapted to alternatively seal the valve inlet and the valve exhaust.

WO 2017/077029 A1 relates to a pump arrangement that is configured to be used with a double breast pump device. The pump arrangement comprises a first terminal and a second terminal for connection to a first expression kit and a second expression kit, respectively. Further, the pump arrangement comprises a plurality of conduits, a suction valve connected to the pump by a connection conduit and to the first and second terminals by respective air conduits, and a venting valve connected to the first and second terminals by venting conduits, wherein the venting valve comprises an opening to the environment. The pump is alternatingly connected to the first and second terminals by alternate opening and closing of the suction valve and the venting valve.

In the field of breast pump devices, there is always a need for compactness of design and reduction of weight in view of the fact that breast pump devices are more often than not used as portables. Another need is to reduce consumption of electric energy. The present invention is in the context of those particular needs and is therefore aimed at providing a way of downsizing breast pump devices, especially downsizing the pump arrangement of breast pump devices, and/or a way of saving energy.

SUMMARY OF THE INVENTION

According to the invention, a pump arrangement is provided that is configured to be used with a double breast pump device comprising two expression kits, each expression kit being designed to subject a breast of a user of the device to a pressure profile and to receive milk expressed from the breast. The pump arrangement comprises:
a pump configured to create the pressure profile in the expression kits, and a first air conduit and a second air conduit, each air conduit being designed to allow for air connection of an expression kit to the pump arrangement, wherein the first air conduit is connectable to and disconnectable from a suction side of the pump through a first suction switching mechanism, wherein the first air conduit is connectable to and disconnectable from a discharge side of the pump through a first discharge switching mechanism, wherein the second air conduit is connectable to and disconnectable from the suction side of the pump through a second suction switching mechanism, wherein the second air conduit is connectable to and disconnectable from the discharge side of the pump through a second discharge switching mechanism, and wherein the first air conduit and the second air conduit are connectable to and disconnectable from each other directly through an intermediate switching mechanism arranged between the air conduits at a bypass position with respect to the pump.

In the pump arrangement according to the invention, the first air conduit and the second air conduit have a function in coupling a first expression kit and a second expression kit, respectively, to the pump. In particular, both air conduits are arranged so as to be connectable to and disconnectable from the suction side of the pump and the discharge side of the pump, through respective switching mechanisms. Further, in the pump arrangement according to the invention, it is possible to make a direct air connection between the air conduits at a bypass position with respect to the pump, i.e. an air connection other than an indirect air connection through the pump, namely by putting a switching mechanism arranged between the air conduits to a position for enabling a direct air connection between the first air conduit and the second air conduit at a bypass position with respect to the pump.

The invention is based on the insight that in the case of a double breast pump device, it is possible to use the volume of the one expression kit as a storage volume of underpressure that can be applied to the other expression kit, and the other way around, assuming that the expression kits are alternatingly addressed during operation of the pump arrangement, as known from WO 2017/077029 A1. Contrary to what is known from the art, when the invention is applied, not all of the reduced pressure created in the expression kits is continually vented to the environment and therefore lost during the vacuum cycle. The fact is that according to the invention, at least part of the underpressure of the one expression kit is transferred to the other expression kit at the moment in the vacuum cycle that it is needed to release the pressure in the one expression kit while creating a vacuum in the other expression kit. Thus, in a process of realizing underpressure in an expression kit, air is not only drawn from the expression kit under the influence of the pump, but also through direct air communication with the other expression kit. In this way, the pump is supported in the function of realizing the vacuum cycle and can be chosen so as to be smaller and cheaper. In any case, there is no need for two or more pumps: one relatively small pump is sufficient for creating the vacuum cycle as desired.

By reusing energy from one expression kit in another, it might further be possible to obtain steeper pressure profiles on the basis of the fact that using two expression kits as each other's vacuum buffer allows for generating a sharper reduction of pressure in an expression kit than could be done by only using a pump. Also, if a battery is used for providing power to the pump, the lifetime of the battery may be increased and/or the battery may be chosen so as to be smaller. In view of the fact that the pump is not addressed to the same extent as would be the case in a conventional situation in which all of the vacuum is continually released to the environment, it is to be concluded that application of the invention also may be beneficial to a long lifetime of the pump.

In a practical embodiment, the pump arrangement according to the invention comprises an intermediate air conduit in which the intermediate switching mechanism is arranged, one side of the intermediate air conduit being connected to the first air conduit, and another side of the intermediate air conduit being connected to the second air conduit, wherein the intermediate switching mechanism is configured to enable variation between an opened condition and a blocked condition of the intermediate air conduit. An intermediate air conduit as mentioned may be connected to the first air conduit at a side of the first air conduit associated with the pump, and, likewise, to the second air conduit at a side of the second air conduit associated with the pump. As long as the intermediate switching mechanism is in a position for enabling a blocked condition of the intermediate air conduit, the first air conduit and the second air conduit can be connected to and disconnected from the pump at appropriate sides of the pump for being charged with underpressure and releasing underpressure, respectively. When the intermediate air conduit is opened, a direct connection between the first air conduit and the second air conduit is obtained, as a short circuit between the first air conduit and the second air conduit, as it were. As a result, an additional air displacement effect is obtained, wherein particularly a natural air flow from an expression kit at a higher pressure to an expression kit at a lower pressure takes place, so that the pressure in the first-mentioned expression kit is more rapidly reduced than as would be the case when only the pump would be used for creating a pressure reduction in that expression kit.

In the pump arrangement according to the invention, at least one resistance may be arranged in at least one of the air conduits of the pump arrangement. By having a resistance in an air conduit, it is possible to determine the speed of an airflow through that air conduit, and thus the speed at which pressure can be reduced or increased through the air conduit. The at least one resistance may be controllable so as to allow the extent to which an airflow is resisted to be set according to desire. On the basis thereof, it is possible to offer various modes of operating a breast pump device to a user.

Many practical embodiments of the pump arrangement according to the invention are feasible. For example, in view of the compactness of design as desired, it may be preferred to have a configuration in which the first suction switching mechanism and the second suction switching mechanism are combined in a single unit such as a single solenoid with two connections.

The respective switching mechanisms may be realized in any suitable practical manner. For example, it is possible for the respective switching mechanisms to comprise a solenoid valve, which is a reliable type of valve that can be accurately controlled.

It follows from the preceding general explanation of the invention that it may be advantageous for the pump arrangement according to the invention to comprise a controller that is configured to control operation of the pump arrangement according to the following repetitive algorithm of successive steps:

setting a condition of the pump arrangement in which the first suction switching mechanism is in a position for connecting the first air conduit to the suction side of the pump, the first discharge switching mechanism is in a position for disconnecting the first air conduit from the discharge side of the pump, the second suction switching mechanism is in a position for disconnecting the second air conduit from the suction side of the pump, the second discharge switching mechanism is in a position for connecting the second air conduit to the discharge side of the pump, and the intermediate switching mechanism is in a position for disabling a direct air connection between the first air conduit and the second air conduit at a bypass position with respect to the pump;

setting a condition of the pump arrangement in which the first suction switching mechanism is in a position for disconnecting the first air conduit from the suction side of the pump, the first discharge switching mechanism is in a position for disconnecting the first air conduit from the discharge side of the pump, the second suction switching mechanism is in a position for disconnecting the second air conduit from the suction side of the pump, the second discharge switching mechanism is in a position for disconnecting the second air conduit from the discharge side of the pump, and the intermediate switching mechanism is in a position for enabling a direct air connection between the first air conduit and the second air conduit at a bypass position with respect to the pump;

setting a condition of the pump arrangement in which the first suction switching mechanism is in a position for disconnecting the first air conduit from the suction side of the pump, the first discharge switching mechanism is in a position for connecting the first air conduit to the discharge side of the pump, the second suction switching mechanism is in a position for connecting the second air conduit to the suction side of the pump, the second discharge switching mechanism is in a position for disconnecting the second air conduit from the discharge side of the pump, and the intermediate switching mechanism is in a position for disabling a direct air connection between the first air conduit and the second air conduit at a bypass position with respect to the pump; and setting a condition of the pump arrangement in which the first suction switching mechanism is in a position for disconnecting the first air conduit from the suction side of the pump, the first discharge switching mechanism is in a position for disconnecting the first air conduit from the discharge side of the pump, the second suction switching mechanism is in a position for disconnecting the second air conduit from the suction side of the pump, the second discharge switching mechanism is in a position for disconnecting the second air conduit from the discharge side of the pump, and the intermediate switching mechanism is in a position for enabling a direct air connection between the first air conduit and the second air conduit at a bypass position with respect to the pump.

The successive steps as defined in the foregoing can be denoted as being a first step of creating a vacuum in a first expression kit and releasing a vacuum in a second expression kit under the influence of the pump, a second step of turning the situation around by first establishing a short circuit between the first expression kit and the second expression kit, as a result of which the vacuum in the first expression kit is released to some extent and a vacuum is created in the second expression kit to some extent, a third step of further releasing the vacuum in the first expression kit and further creating a vacuum in the second expression kit under the influence of the pump, and a fourth step of turning the situation around again by first establishing a short circuit between the first expression kit and the second expression kit, as a result of which a vacuum in the first expression kit is created to some extent and the vacuum is released in the second expression kit to some extent. The fourth step is followed by the first step in order to further create a vacuum in the first expression kit and to further release the vacuum in the second expression kit under the influence of the pump before the situation is turned around again in the second step, etc.

The pump arrangement according to the invention may be equipped with at least one pressure sensor arranged and configured to determine when the pressure has reached a certain threshold and a switch is to be made from a step in which the intermediate switching mechanism is in a position for enabling a direct air connection between the first air conduit and the second air conduit at a bypass position with respect to the pump to a subsequent step. Such a pressure sensor may be part of a general control system of the pump arrangement that comprises the controller as mentioned earlier.

In a similar manner as known from WO 2017/077029 A1, the pump arrangement according to the invention may comprise a first connection terminal associated with an end of the first air conduit and being designed to function as a connecting interface between an expression kit and the first air conduit, and a second connection terminal associated with an end of the second air conduit and being designed to function as a connecting interface between an expression kit and the second air conduit, as one possible way of facilitating the necessary air connection between two expression kits and the pump arrangement. It is very practical if the pump arrangement according to the invention is accommodated in a vacuum unit of a double breast pump device comprising two expression kits that are connectable to and disconnectable from the vacuum unit. In such a case, assuming that the pump arrangement comprises the connection terminals as mentioned, the connection terminals may be arranged so as to be accessible at an outside wall of a housing of the vacuum unit.

The invention also provides a double breast pump device, comprising two expression kits, each expression kit being designed to subject a breast of a user of the device to a pressure profile and to receive milk expressed from the breast, and a pump arrangement as described in the foregoing. In conformity with what has been indicated earlier, the double breast pump device may comprise a vacuum unit, in which case it is practical if the expression kits are connectable to and disconnectable from the vacuum unit, and the pump arrangement is accommodated in the vacuum unit.

The invention further relates to a method of operating a pump arrangement of a double breast pump device comprising two expression kits, each expression kit being designed to subject a breast of a user of the device to a pressure profile and to receive milk expressed from the breast, the pump arrangement comprising a pump configured to create the pressure profile in the expression kits, and a first air conduit and a second air conduit, each air conduit being designed to allow for air connection of an expression kit to the pump arrangement, each air conduit being connectable to and disconnectable from a suction side and a discharge side, respectively, of the pump, and the first air conduit and the second air conduit being connectable to and disconnectable from each other directly at a bypass position with respect to the pump, the method comprising repeating the following successive steps:

setting a condition of the pump arrangement in which the first air conduit is connected to the suction side of the pump and disconnected from the discharge side of the pump, the second air conduit is disconnected from the suction side of the pump and connected to the discharge side of the pump, and direct air connection between the first air conduit and the second air conduit at a bypass position with respect to the pump is disabled;

setting a condition of the pump arrangement in which the first air conduit is disconnected from both the suction side and the discharge side of the pump, the second air conduit is disconnected from both the suction side and the discharge side of the pump, and direct air connection between the first air conduit and the second air conduit at a bypass position with respect to the pump is enabled;

setting a condition of the pump arrangement in which the first air conduit is disconnected from the suction side of the pump and connected to the discharge side of the pump, the second air conduit is connected to the suction side of the pump and disconnected from the discharge side of the pump, and direct air connection between the first air conduit and the second air conduit at a bypass position with respect to the pump is disabled; and setting a condition of the pump arrangement in which the first air conduit is disconnected from both the suction side and the discharge side of the pump, the second air conduit is disconnected from both the suction side and the discharge side of the pump, and direct air connection between the first air conduit and the second air conduit at a bypass position with respect to the pump is enabled.

As noted earlier, the successive steps as defined in the foregoing can be denoted as being a first step of creating a vacuum in a first expression kit and releasing a vacuum in a second expression kit under the influence of the pump, a second step of turning the situation around by first allowing for direct exchange of air between the first expression kit and the second expression kit, as a result of which the vacuum in the first expression kit is released to some extent and a vacuum is created in the second expression kit to some extent, a third step of further releasing the vacuum in the first expression kit and further creating a vacuum in the second expression kit under the influence of the pump, and a fourth step of turning the situation around again by first allowing for a direct exchange of air between the first expression kit and the second expression kit, as a result of which a vacuum in the first expression kit is created to some extent and the vacuum is released in the second expression kit to some extent. The fourth step is followed by the first step in order to further create a vacuum in the first expression kit and to further release the vacuum in the second expression kit under the influence of the pump before the situation is turned around again in the second step, etc.

The above-described and other aspects of the invention will be apparent from and elucidated with reference to the following detailed description of a breast pump device and particularly a pump arrangement of the breast pump device.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
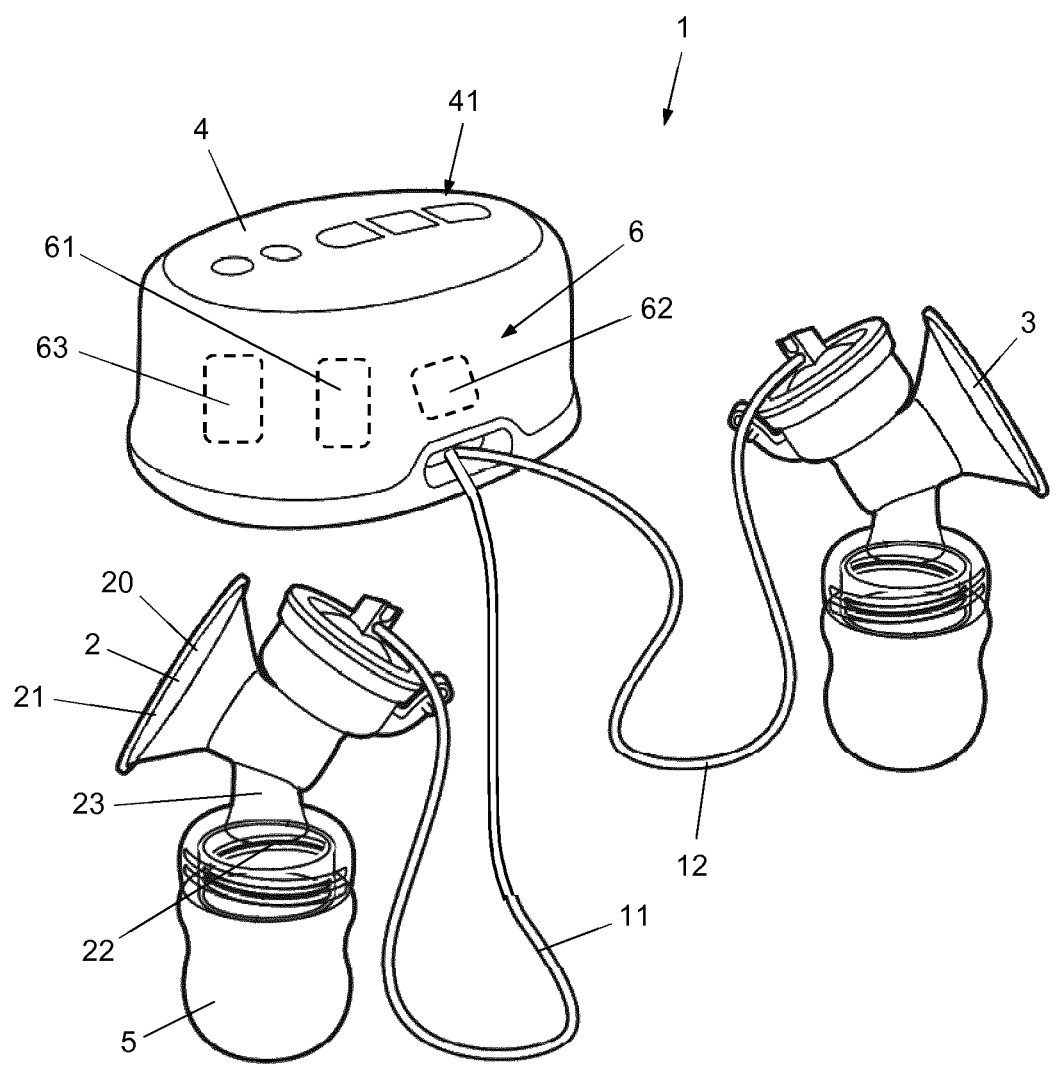
FIG. 1 diagrammatically shows a breast pump device comprising a vacuum unit, two expression kits, and two flexible air hoses interconnecting the vacuum unit and the respective expression kits.

The invention is in the field of breast pump devices, particularly electric breast pump devices, more particularly electric double breast pump devices. With reference to FIG. 1, a general description of an electric double breast pump device will be given so as to generate a clear picture of the context in which the invention is applicable.

The breast pump device 1 comprises two expression kits 2, 3 and a vacuum unit 4 for generating a pressure cycle during which vacuum is alternatingly created and released, for which reason the pressure cycle is also referred to as vacuum cycle. The expression kits 2, 3 are both connectable to the vacuum unit 4 which is therefore a common vacuum unit 4 to the expression kits 2, 3. Each of the expression kits 2, 3 comprises a functional expression body 20 and a milk receptacle 5 that is connectable to the expression body 20, e.g. by screwing, thereby closing a lower end of the expression body 20. It is also possible that a single milk receptacle 5 is used for receiving milk from both expression kits 2, 3. The vacuum unit 4 is an electric vacuum unit and comprises a pump arrangement 6 including an electric pump 61 and an air valve 62 for realizing the vacuum cycle as mentioned during operation, i.e. during pumping sessions to be performed by means of the breast pump device 1. The pump 61, the air valve 62 and an associated controller 63 for realizing proper operation of the pump arrangement 6 are designed to function in a manner that is well known in the field of breast pump devices. Therefore, further details of these components will not be further explained in the present text, and the same is applicable to other practical aspects of the vacuum unit 4 known per se. For the same reason, the pump 61, the air valve 62 and the controller 63 are only diagrammatically depicted in FIG. 1 as dashed rectangles.

The vacuum unit 4 may accommodate a battery or other means for providing electric power to the various components of the vacuum unit 4 during a pumping session. Alternatively or additionally, it is possible for the vacuum unit 4 to be equipped with an electric cord for connection of the vacuum unit 4 to an external source of electric power, which electric cord may be fixed to the vacuum unit 4 or detachably connected to the vacuum unit 4. Further, the vacuum unit 4 may be provided with a user interface 41 for allowing a user of the vacuum unit 4 to influence operational parameters such as suction force, pumping frequency, and variation of the suction force over time. In general, a user interface 41 may be realized in any suitable manner such as through a number of buttons as illustrated in FIG. 1, or through a touch screen, for example.

Advantageously, the pump arrangement 6 is designed to create a vacuum in the expression kits 2, 3 to be used with the vacuum unit 4 in an alternating fashion, so that it is sufficient to have only one pump 61 in the pump arrangement 6. A system of valves such as known from WO 2017/077029 A1 may be used to enable operation of the breast pump device 1 in which the two expression kits 2, 3 are alternatingly put under the influence of the pump 61 and the air valve 62, so that the creation and the release of vacuum takes place in one of the expression kits 2, 3 at a time, while as seen through time, the breasts of a user of the breast pump device 1 are equally addressed.

The expression body 20 comprises a breast-receiving funnel 21, an aperture acting as a milk outlet 22, and a milk path 23 from the breast-receiving funnel 21 to the milk outlet 22. The breast-receiving funnel 21 is thus in fluid communication with the milk outlet 22 through the milk path 23. The breast-receiving funnel 21 can comprise a massage cushion or the like (not shown) for providing a soft and warm feel to the breast and/or imitating a baby's sucking action.

In FIG. 1, the breast pump device 1 is shown in an assembled condition, in which the vacuum unit 4 is connected to the expression kits 2, 3 through respective flexible air hoses 11, 12. Such a configuration allows for a remote arrangement of the vacuum unit 4 with respect to the expression kits 2, 3, so that the size of that part of the breast pump device 1 that is to be applied to a user's breast can be kept within reasonable limits.

During operation of the breast pump device 1 as described, due to the two expression kits 2, 3 being alternatingly put under the influence of the pump 61 and the air valve 62, it happens that maximum suction force is applied in the one expression kit 2, 3 while the other expression kit 2, 3 is vented. The fact is that the pump 61 continuously generates underpressure, and that the system of valves is controlled for the purpose of realizing a sequence in which an air connection between the pump 61 and the air valve 62 and a first expression kit 2 is established first, while a second expression kit 3 is disconnected from the pump 61 and the air valve 62 and is allowed to vent to the environment, and in which an air connection between the pump 61 and the air valve 62 and the second expression kit 3 is established later, while the first expression kit 2 is allowed to vent to the environment, which sequence is continuously repeated during operation.

Figure 2:
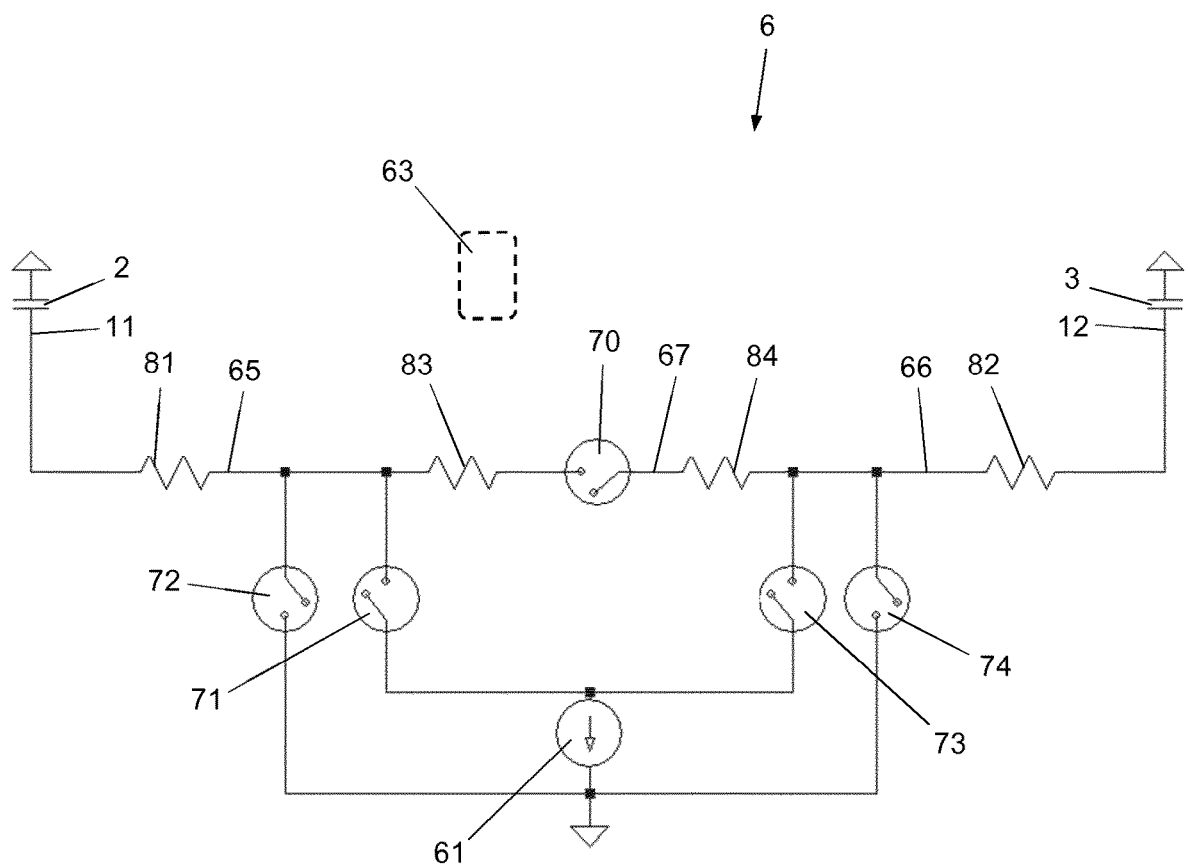
FIG. 2 is a schematic of the set-up of a pump arrangement according to the invention, as may be used in a double breast pump device, and further diagrammatically shows two expression kits connected to the pump arrangement.

FIG. 2 serves to illustrate the set-up of a pump arrangement 6 according to the invention, as may be used in a double breast pump device 1. Besides providing a diagrammatic representation of components of the pump arrangement 6 and their positioning with respect to each other, FIG. 2 further illustrates two expression kits 2, 3 connected to the pump arrangement 6.

Besides a pump 61 that is intended to create a pressure profile as desired in the expression kits 2, 3, and a controller 63 that is configured to control operation of the pump arrangement 6, the pump arrangement 6 comprises a system of air conduits 65, 66, 67 and a number of switching mechanisms 70, 71, 72, 73, 74 arranged at useful positions as will now be explained. In respect of the pump 61, it is noted that as is usual in the field of pumps used for displacing air, the pump 61 has a suction side where air is let in to the pump 61 during operation of the pump 61 and a discharge side where air is discharged from the pump 61 during operation of the pump 61.

The pump arrangement 6 according to the invention comprises a first air conduit 65 and a second air conduit 66, each air conduit 65, 66 being designed to allow for air connection of an expression kit 2, 3 to the pump arrangement 6. In a practical situation, assuming that the pump arrangement 6 is located in a vacuum unit 4, the air conduits 65, 66 of the pump arrangement 6 extend inward from respective connecting interfaces which are accessible at the outside of the vacuum unit 4 and which are designed to enable the flexible air hoses 11, 12 extending from the respective expression kits 2, 3 to be interconnected with the respective air conduits 65, 66. In the following description, it is assumed that a first expression kit 2 is connected to the first air conduit 65 and that a second expression kit 3 is connected to the second air conduit 66.

The pump arrangement 6 comprises four switching mechanisms 71, 72, 73, 74 arranged and configured to either connect the air conduits 65, 66 and thus the expression kits 2, 3 to one of the suction side and the discharge side of the pump 61 or disconnect the air conduits 65, 66 and thus the expression kits 2, 3 from one of the suction side and the discharge side of the pump 61. In particular, the arrangement and configuration of the respective switching mechanisms 71, 72, 73, 74 is chosen such that a first suction switching mechanism 71 is suitable to be used for setting a connection status of the first air conduit 65 with respect to the suction side of the pump 61, a first discharge switching mechanism 72 is suitable to be used for setting a connection status of the first air conduit 65 with respect to the discharge side of the pump 61, a second suction switching mechanism 73 is suitable to be used for setting a connection status of the second air conduit 66 with respect to the suction side of the pump 61, and a second discharge switching mechanism 74 is suitable to be used for setting a connection status of the second air conduit 66 with respect to the discharge side of the pump 61.

Further, the pump arrangement 6 comprises a fifth switching mechanism 70 that is arranged in an intermediate air conduit 67 extending between the first air conduit 65 and the second air conduit 66. In the shown example, the intermediate air conduit 67 is connected to the first air conduit 65 at a side of the first air conduit 65 associated with the pump 61, and the intermediate air conduit 67 is connected to the second air conduit 66 at a side of the second air conduit 66 associated with the pump 61. In a general sense, according to an important aspect of the invention, a means or mechanism is provided for enabling a direct connection between the first air conduit 65 and the second air conduit 66, i.e. a connection that is not a connection through the pump 61, as a kind of short circuit between the air conduits 65, 66, so as to realize a direct exchange of air between expression kits 2, 3 when appropriate during operation of the breast pump device 1. The configuration illustrated in FIG. 2 only reflects one of various practical possibilities.

On the basis of the design of the pump arrangement 6 with the various air conduits 65, 66, 67 and the various switching mechanisms 70, 71, 72, 73, 74, it is possible to realize different air paths through the pump arrangement 6, depending on the settings of the switching mechanisms 70, 71, 72, 73, 74. A practical way of controlling the pump arrangement 6 during operation thereof involves a repetition of the following four successive steps:

1) having the first suction switching mechanism 71 and the second discharge switching mechanism 74 in an air flow enabling position, and having the other switching mechanisms 70, 72, 73 in an air flow blocking position, so that the pressure in a first expression kit 2 may be reduced while the pressure in a second expression kit 3 increases under the influence of the pump 61, 2) having only the intermediate switching mechanism 70 in an air flow enabling position, and having all other switching mechanisms 71, 72, 73, 74 in an air flow blocking position, so that direct air exchange between the expression kits 2, 3 is possible and the pressures prevailing in the expression kits 2, 3 are automatically adjusted without needing to address the pump 61, wherein the pressure in the first expression kit 2 increases and the pressure in the second expression kit 3 decreases, 3) having the first discharge switching mechanism 72 and the second suction switching mechanism 73 in an air flow enabling position, and having the other switching mechanisms 70, 71, 74 in an air flow blocking position, so that the pressure in the first expression kit 2 may be further increased while the pressure in the second expression kit 3 may be further reduced under the influence of the pump 61, and 4) having only the intermediate switching mechanism 70 in an air flow enabling position, and having all other switching mechanisms 71, 72, 73, 74 in an air flow blocking position, as is the case in the second step, so that direct air exchange between the expression kits 2, 3 is possible and the pressures prevailing in the expression kits 2, 3 are automatically adjusted without needing to address the pump 61, wherein the pressure in the first expression kit 2 decreases and the pressure in the second expression kit 3 increases.

It is possible for the pump arrangement 6 to be equipped with at least one pressure sensor for determining when the pressure has reached a certain threshold and a switch can be made from a step of precharging the one expression kit 2, 3 with vacuum from the other expression kit 2, 3 to a subsequent step. Alternatively, it is possible to apply open loop control and to automatically make the switch on the basis of preset parameters. Further, one or more resistances may be added to one or more air conduits 65, 66, 67 of the pump arrangement 6. By way of example, FIG. 2 illustrates the use of a resistance 81 in the first air conduit 65, a resistance 82 in the second air conduit 66, and two resistances 83, 84 in the intermediate conduit 67, on either side of the intermediate switching mechanism 70. By having one or more resistances in an air conduit 65, 66, 67, it is achieved that a speed at which pressure is reduced or released in an expression kit 2, 3 can be influenced. In a sophisticated embodiment of the pump arrangement 6, the one or more resistances may be controllable.

When the above sequence is followed, it is achieved that every time it is intended to address another expression kit 2, 3 for the purpose of creating a vacuum, the operation of the pump 61 is supported on the basis of the fact that pressure reduction in the expression kit 2, 3 in question is already realized to some extent as a result of a preceding step that involves establishing a direct connection between the first air conduit 65 and the second air conduit 66 to which the respective expression kits 2, 3 are connected. The energy provided by the pump 61 is very efficiently used on the basis of this fact that an operational sequence aimed at using the vacuum in one of the expression kits 2, 3 in the process of creating a vacuum in another of the expression kits 2, 3 is continually repeated. The expression kits 2, 3 are not just alternatingly subjected to a vacuum creating action, but are also alternatingly made to function as each other's vacuum buffers. As one of the important advantageous results of this way of doing, it is possible to use only one relatively small pump 61 in the pump arrangement 6. In this way, both space and costs can be saved.

A summary of the invention may read as follows. In a pump arrangement 6 for use with a double breast pump device 1, a first air conduit 65 and a second air conduit 66 have a function in connecting respective expression kits 2, 3 to the pump arrangement 6. Each of the air conduits 65, 66 is connectable to and disconnectable from a suction side and a discharge side, respectively, of a pump 61 that is included in the pump arrangement 6. Further, the air conduits 65, 66 are connectable to and disconnectable from each other directly through an intermediate switching mechanism 70 arranged between the air conduits 65, 66 at a bypass position with respect to the pump 61, so that it is possible to directly transfer vacuum between the air conduits 65, 66 and to thereby support the functioning of the pump 61. Among other things, the pump 61 can be chosen to be smaller than as would be necessary without the possibility of establishing a direct connection between the air conduits 65, 66.

The invention claimed is:

1. A pump arrangement, configured to be used with a double breast pump device comprising two expression kits, each expression kit being designed to subject a breast of a user of the double breast pump device to a pressure profile and to receive milk expressed from the breast, the pump arrangement comprising:
    a pump configured to create the pressure profile in the expression kits, and
    a first air conduit and a second air conduit, each air conduit being designed to allow for air connection of a respective expression kit to the pump arrangement,
    wherein the first air conduit is connectable to and disconnectable from a suction side of the pump through a first suction switching mechanism,
    wherein the first air conduit is connectable to and disconnectable from a discharge side of the pump through a first discharge switching mechanism,
    wherein the second air conduit is connectable to and disconnectable from the suction side of the pump through a second suction switching mechanism,
    wherein the second air conduit is connectable to and disconnectable from the discharge side of the pump through a second discharge switching mechanism, and
    wherein the first air conduit and the second air conduit are connectable to and disconnectable from each other directly through an intermediate switching mechanism arranged between the air conduits at a bypass position with respect to the pump.

2. The pump arrangement according to claim 1, wherein the pump arrangement comprises an intermediate air conduit in which the intermediate switching mechanism is arranged, one side of the intermediate air conduit being connected to the first air conduit, and another side of the intermediate air conduit being connected to the second air conduit, wherein the intermediate switching mechanism is configured to enable variation between an opened condition and a blocked condition of the intermediate air conduit.

3. The pump arrangement according to claim 2, wherein the intermediate air conduit is connected to the first air conduit at a side of the first air conduit associated with the pump, and wherein the intermediate air conduit is connected to the second air conduit at a side of the second air conduit associated with the pump.

4. The pump arrangement according to claim 1, wherein at least one resistance is arranged in at least one of the first air conduit is replaced with the first air conduit or the second air conduit of the pump arrangement.

5. The pump arrangement according to claim 4, wherein the at least one resistance is controllable.

6. The pump arrangement according to claim 1, wherein the first suction switching mechanism and the second suction switching mechanism are combined in a single unit that is connected to the suction side of the pump, the first air conduit and the second air conduit, respectively, and that includes a first way between the suction side of the pump and the first air conduit and a second way between the suction side of the pump and the second air conduit.

7. The pump arrangement according to claim 1, wherein the respective switching mechanisms comprise a solenoid valve.

8. The pump arrangement according to claim 1, wherein the pump arrangement comprises a controller configured to control operation of the pump arrangement according to the following repetitive algorithm of successive steps:

setting a condition of the pump arrangement in which the first suction switching mechanism is in a position for connecting the first air conduit to the suction side of the pump, the first discharge switching mechanism is in a position for disconnecting the first air conduit from the discharge side of the pump, the second suction switching mechanism is in a position for disconnecting the second air conduit from the suction side of the pump, the second discharge switching mechanism is in a position for connecting the second air conduit to the discharge side of the pump, and the intermediate switching mechanism is in a position for disabling a direct air connection between the first air conduit and the second air conduit at a bypass position with respect to the pump;

setting a condition of the pump arrangement in which the first suction switching mechanism is in a position for disconnecting the first air conduit from the suction side of the pump, the first discharge switching mechanism is in the position for disconnecting the first air conduit from the discharge side of the pump, the second suction switching mechanism is in a position for disconnecting the second air conduit from the suction side of the pump, the second discharge switching mechanism is in a position for disconnecting the second air conduit from the discharge side of the pump, and the intermediate switching mechanism is in a position for enabling a direct air connection between the first air conduit and the second air conduit at a bypass position with respect to the pump;

setting a condition of the pump arrangement in which the first suction switching mechanism is in a position for disconnecting the first air conduit from the suction side of the pump, the first discharge switching mechanism is in the position for connecting the first air conduit to the discharge side of the pump, the second suction switching mechanism is in the position for connecting the second air conduit to the suction side of the pump, the second discharge switching mechanism is in a position for disconnecting the second air conduit from the discharge side of the pump, and the intermediate switching mechanism is in a position for disabling a direct air connection between the first air conduit and the second air conduit at the bypass position with respect to the pump; and setting a condition of the pump arrangement in which the first suction switching mechanism is in the position for disconnecting the first air conduit from the suction side of the pump, the first discharge switching mechanism is in a position for disconnecting the first air conduit from the discharge side of the pump, the second suction switching mechanism is in a position for disconnecting the second air conduit from the suction side of the pump, the second discharge switching mechanism is in the position for disconnecting the second air conduit from the discharge side of the pump, and the intermediate switching mechanism is in the position for enabling a direct air connection between the first air conduit and the second air conduit at the bypass position with respect to the pump.

9. The pump arrangement according to claim 8, wherein the pump arrangement comprises at least one pressure sensor arranged and configured to determine when the pressure has reached a certain threshold and a switch is to be made from one of the successive steps in which the intermediate switching mechanism is in a position for enabling a direct air connection between the first air conduit and the second air conduit at the bypass position with respect to the pump to a subsequent step.

10. The pump arrangement according to claim 1, wherein the pump arrangement comprises a first connection terminal associated with an end of the first air conduit and being designed to function as a connecting interface between one of the expression kits and the first air conduit, and a second connection terminal associated with an end of the second air conduit and being designed to function as a connecting interface between another one of the expression kits and the second air conduit.

11. The pump arrangement according to claim 1, wherein the pump arrangement is accommodated in a vacuum unit of the double breast pump device comprising two expression kits that are connectable to and disconnectable from the vacuum unit.

12. A double breast pump device (1), comprising
two expression kits, each expression kit being designed to subject the breast of the user of the device to the pressure profile and to receive milk expressed from the breast, and
the pump arrangement according to claim 1.

13. The double breast pump device according to claim 12, wherein the double breast pump device comprises a vacuum unit, the expression kits being connectable to and disconnectable from the vacuum unit, and the pump arrangement being accommodated in the vacuum unit.

14. A method of operating a pump arrangement of a double breast pump device comprising two expression kits, each expression kit being designed to subject a breast of a user of the device to a pressure profile and to receive milk expressed from the breast, the pump arrangement comprising a pump configured to create the pressure profile in the expression kits, and a first air conduit and a second air conduit, each air conduit being designed to allow for air connection of an expression kit to the pump arrangement, characterized in that each air conduit being is connectable to and disconnectable from a suction side and a discharge side, respectively, of the pump, and the first air conduit and the second air conduit are connectable to and disconnectable from each other directly at a bypass position with respect to the pump, the method comprising repeating the following successive steps:

setting a condition of the pump arrangement in which the first air conduit is connected to the suction side of the pump and disconnected from the discharge side of the pump, the second air conduit is disconnected from the suction side of the pump and connected to the discharge side of the pump, and direct air connection between the first air conduit and the second air conduit at the bypass position with respect to the pump is disabled;

setting a condition of the pump arrangement in which the first air conduit is disconnected from both the suction side and the discharge side of the pump, the second air conduit is disconnected from both the suction side and the discharge side of the pump, and direct air connection between the first air conduit and the second air conduit at the bypass position with respect to the pump is enabled;

setting a condition of the pump arrangement in which the first air conduit is disconnected from the suction side of the pump and connected to the discharge side of the pump, the second air conduit is connected to the suction side of the pump and disconnected from the discharge side of the pump, and direct air connection between the first air conduit and the second air conduit at the bypass position with respect to the pump is disabled; and setting a condition of the pump arrangement in which the first air conduit is disconnected from both the suction side and the discharge side of the pump, the second air conduit is disconnected from both the suction side and the discharge side of the pump, and direct air connection between the first air conduit and the second air conduit at the bypass position with respect to the pump is enabled.

* * * * *